US011517686B2

(12) United States Patent
Esteve (10) Patent No.: US 11,517,686 B2
(45) Date of Patent: Dec. 6, 2022

(54) DRY POWDER INHALER

(71) Applicant: Emphasys Importadora Exportadora e Distribuidora Ltda., Porto Feliz Sp (BR)

(72) Inventor: Victor Esteve, Itu (BR)

(73) Assignee: Emphasys Importadora Exportadora e Distribuidora Ltda., Porto Feliz Sp (BR)

( * ) Notice: Subject to any disclaimer, the term of this patent is extended or adjusted under 35 U.S.C. 154(b) by 690 days.

(21) Appl. No.: 16/470,793

(22) PCT Filed: Dec. 20, 2016

(86) PCT No.: PCT/IB2016/001789
§ 371 (c)(1),
(2) Date: Jun. 18, 2019

(87) PCT Pub. No.: WO2018/115915
PCT Pub. Date: Jun. 28, 2018

(65) Prior Publication Data
US 2019/0344025 A1 Nov. 14, 2019

(51) Int. Cl.
*A61M 15/00* (2006.01)
*A61M 11/00* (2006.01)

(52) U.S. Cl.
CPC ...... *A61M 15/0023* (2014.02); *A61M 11/003* (2014.02); *A61M 15/0035* (2014.02);
(Continued)

(58) Field of Classification Search
CPC ............ A61M 15/0023; A61M 11/003; A61M 15/0035; A61M 15/0041;
(Continued)

(56) References Cited

U.S. PATENT DOCUMENTS 3,837,341 A 9/1974 Bell
3,918,451 A * 11/1975 Steil .................... A61M 15/004
128/203.21
(Continued)

FOREIGN PATENT DOCUMENTS

CN 101384288 A 3/2009
EP 3138600 A1 3/2017
(Continued)

OTHER PUBLICATIONS

Chinese Office Action issued in corresponding Chinese Application No. 201680091716.4 dated Jul. 14, 2021.
(Continued)

*Primary Examiner* — Justine R Yu
*Assistant Examiner* — Matthew R Moon
(74) *Attorney, Agent, or Firm* — Carter, DeLuca & Farrell LLP (57) ABSTRACT

A dry powder inhaler for a capsule containing dry powder, the inhaler comprising a housing having a capsule receptacle, two actuator buttons arranged on opposing sides of the housing and two perforation needles, each needle being fixedly connected to an actuator button and movable relative to the housing towards each other from a normal position to a perforation position along an actuation direction to perforate a capsule arranged in the capsule receptacle, wherein a first end of each actuator button is connected to the housing at a lower portion of the housing and in that a second free end of each actuator button is movable into the perforation position such that the perforation needle is moved along a circular line.

23 Claims, 10 Drawing Sheets

(52) U.S. Cl.
CPC ... *A61M 15/0041* (2014.02); *A61M 2202/064* (2013.01); *A61M 2206/16* (2013.01)

(58) Field of Classification Search
CPC ........ A61M 2202/064; A61M 2206/16; A61M 15/003; A61M 15/0006
See application file for complete search history.

(56) References Cited

U.S. PATENT DOCUMENTS

| | | | |
|---|---|---|---|
| 4,689,455 A | | 8/1987 | Watanabe |
| 4,884,565 A | * | 12/1989 | Cocozza ........... A61M 15/0028 128/203.15 |
| 5,797,391 A | * | 8/1998 | Cook ................ A61M 15/0028 128/203.15 |
| 8,479,730 B2 | | 7/2013 | Ziegler et al. |
| 2003/0000523 A1 | | 1/2003 | Citterio |
| 2006/0181517 A1 | * | 8/2006 | Zadesky ............... G06F 3/0362 345/173 |
| 2007/0295332 A1 | * | 12/2007 | Ziegler ............. A61M 15/0028 128/203.15 |
| 2013/0276783 A1 | | 10/2013 | Chen et al. |
| 2015/0231344 A1 | | 8/2015 | Deboeck et al. |
| 2016/0158470 A1 | | 6/2016 | Esteve et al. |

FOREIGN PATENT DOCUMENTS

| | | |
|---|---|---|
| EP | 3138601 A1 | 3/2017 |
| WO | 9406498 A1 | 3/1994 |

OTHER PUBLICATIONS

International Search Report and Written Opinion issued in International Application No. PCT/IB2016/001789 dated May 8, 2018, 8 pages.

* cited by examiner

DRY POWDER INHALER

The invention relates to a dry powder inhaler for a capsule containing dry powder, the inhaler comprising a housing having a capsule receptacle, two actuator buttons arranged on opposing sides of the housing and two perforation needles, each needle being fixedly connected to an actuator button and movable relative to the housing towards each other from a normal position to a perforation position along an actuation direction to perforate a capsule arranged in the capsule receptacle. The invention also relates to a dry powder inhaler for a capsule containing dry powder, the inhaler comprising a housing having a base body with a capsule chamber and a covering body connected to the base body, and comprising a mouthpiece covering the capsule chamber and operable for sucking air through the capsule chamber.

Such a dry powder inhaler is known, for example from EP 1 270 034 A1 or from US 2003/0000523. Those dry powder inhalers are typically non-pressurized inhalers. A capsule which is arranged in the capsule receptacle of the dry powder inhaler can be pierced by the needles. When air is sucked in by a patient through a mouthpiece, the capsule is lifted from the capsule receptacle into a capsule chamber and rotates in the capsule chamber. Upon rotation of the capsule, dry powder contained in the capsule is dispersed by centrifugal forces during rotation and mixed with air such that it can be inhaled by a patient.

In order to disperse the dry powder contained in the capsule, the capsule has to be perforated by the needles. Nevertheless, the perforation technique in the prior art inhalers is either complicated to manufacture or needs a lot of moving parts which makes the inhalers difficult to assemble and more expensive.

It is furthermore a problem of the known dry powder inhalers that the dosage of dry powder is limited. When piercing the capsule directly in its hemispherical ends, the amount of powder to be dispersed during inhalation is limited because the flow of the dry powder out of the pierced openings is obstructed during rotational movement of the capsule due to the arrangement of the openings. The obstruction can be caused by cut-out portions of the capsule shell which are cut out by the needles when piercing the capsule and bended towards inside the capsule shell. Moreover, the known dry powder inhalers are limited in the maximum dosage of dry powder. In certain areas of application a high dosage in the range of about 25 to about 200 mg of dry powder is required for treatments or clinical tests for treatment of cystic fibrosis, tuberculosis, pulmonary artery hypertension, neurologic and congenital disorders, Parkinson, asthma, Chronic obstructive pulmonary disease (COPD) etc.

Moreover, known inhalers often have the problem that a big variation in the inhalation resistance can occur depending on the pulmonary capacity of a user or patient, wherein a high inhalation resistance at a typical pulmonary capacity of under about 60 l/min should be avoided.

It is therefore an object of the present invention to provide a cost effective dry powder inhaler for dispersion of dry powder which provides for easy handling and effective delivery of dosages of dry powder without the need for high inhalation resistance.

This object is solved by a dry powder inhaler according to the features of claim 1. Such a dry powder inhaler is characterized in that a first end of each actuator button is connected to the housing at a lower portion of the housing and in that a second free end of each actuator button is movable into the perforation position such that the perforation needle is moved along a circular line. Preferably, the housing is made of two parts, wherein the housing comprises a base body with a capsule chamber and a covering body connected to the base body. With this dry powder inhaler, a cost effective and simple construction can be provided which makes the perforation of a capsule arranged in the capsule receptacle easy to be achieved. By arranging two actuator buttons on opposing sides of the housing and connecting each actuator button to the housing at a lower portion of the housing, wherein a perforation needle is arranged at a second free end of the actuator button, the actuator buttons can be pre-loaded into the normal position by use of only one spring element arranged between the actuator buttons. Therefore, a simple and cost effective construction can be achieved. The capsule receptacle can be arranged in an angle with respect to the actuation direction. Nevertheless, it is also possible that the capsule receptacle is arranged parallel to the actuation direction.

According to a first advantageous embodiment of the inhaler, the first end of each actuator button is pivotably attached to the housing.

It is particularly preferred if the first end of each actuator button is connected to the housing via a ball joint snap-on connection pivoting around a pivot axis. By providing a ball joint snap-on connection, the actuator buttons can be attached to the lower portion of the housing by engaging the ball point snap-on connection.

Advantageously, the actuator buttons are pivotable around a pivoting angle of about 5 to 15°, preferably of about 10°.

In another preferred embodiment of the inhaler, the ball joint snap-on connection comprises hemi-spherical protrusions arranged on the housing and hemi-spherical recesses arranged on the actuator buttons complementary to the hemi-spherical protrusions, wherein the protrusions and recesses extend along the pivot axis. In order to engage the ball joint snap-on connection, the hemi-spherical protrusions are preferably arranged on the housing such that they can be elastically pushed into a release position along the direction of the pivot axis. In the release position, the recesses of the actuator buttons and the protrusions of the housing can be superimposed such that the protrusions can engage the recesses and elastically move back into an engagement position of the ball joint snap-on connection.

It is particularly preferred if the perforation needles are arranged in an area of the second free end of each actuator button spaced away from the first end of the actuator button. Preferably, the perforation needles are arranged on the inside surfaces of the actuator buttons facing each other. By arranging the perforation needles in an area of the second free end of each actuator button, a large movement range can be provided despite connecting a first end of each actuator button to the housing.

In a particularly preferred embodiment, the dry powder inhaler comprises a spring element acting upon the actuator buttons such that the actuator buttons are pre-loaded into the normal position. Preferably, the spring element is a helical spring.

In another preferred embodiment of the dry powder inhaler, the housing comprises two openings configured to receive the actuator buttons such that an outside surface of the housing and the actuator buttons is substantially flush when the actuator buttons are in the normal position. It is particularly preferred if the actuator buttons close the openings in the housing in the normal position in a substantially airtight manner such that no or substantially no air can pass between the actuator buttons and the opening edges.

The object of the subject invention is also solved by a dry powder inhaler according to the features of claim 9. Such a dry powder inhaler is characterized in that capsule receptacle is arranged in an inclined angle within the range of about 40° to about 50° with respect to the actuation direction. Arranging the capsule receptacle in such an inclined manner with respect to the actuation direction provides the advantage that a capsule which can be arranged in the capsule receptacle can be pierced in a transition area of the hemispherical ends and the tubular middle section of the capsule. Preferably, the capsule receptacle is arranged such that a capsule can be pierced in a position that allows powder to be dispersed during the rotational movement in an inhalation process while providing little or almost no obstruction to the powder flow on the way out.

According to a particularly preferred embodiment of the dry powder inhaler, the needles are arranged parallel to the actuation direction and spaced apart from a middle plane of the base body. The middle plane is a plane parallel to a longitudinal axis of the base body which divides the base body into two parts of substantially the same size. By arranging the needles parallel to the actuation direction and spaced apart from the middle plane of the base body, a capsule arranged in the capsule receptacle can be pierced in an angle such that a cut-out portion of the capsule can be bent into the capsule such that it does not obstruct the flow of dry powder during inhalation. Preferably, the needles are arranged on opposing sides of the middle plane. Therefore, upon piercing a capsule arranged in the capsule receptacle, the cut-out portions can be bent inside into the capsule in a flap-like manner.

According to another preferred embodiment, the capsule receptacle is arranged perpendicular to a longitudinal axis of the inhaler.

It is particularly preferred it the base body comprises two hollow needle guiding sections configured to guide the needles, the needle guiding sections being arranged perpendicular to a longitudinal axis of the inhaler and ending in the capsule receptacle. By providing such needle guiding sections the needles can be guided and supported during actuation of the actuator buttons such that a capsule inserted into the capsule receptacle is always pierced in substantially the same position.

According to another advantageous embodiment, the base body is having a capsule chamber for rotation of a capsule. Providing such a capsule chamber has the advantage that a capsule can be lifted into the capsule chamber by sucking air through a mouthpiece of the dry powder inhaler and rotates in the capsule chamber due to air flow generated in the capsule chamber upon inhalation.

Therefore, it is particularly preferred if the capsule receptacle is arranged in the capsule chamber and connected to the capsule chamber.

Preferably, the capsule chamber is having a circular cylindrical section and a conical section, wherein the capsule receptacle is arranged in the conical section.

In a preferred embodiment, the circular cylindrical section of the capsule chamber has a diameter which is bigger than a length of the capsule receptacle. The diameter is preferably chosen such that a capsule can be lifted into the capsule chamber during inhalation and rotates in the capsule chamber.

In order to provide for a rotational movement of the capsule during inhalation it is particularly preferred if the base body is having at least two air inlets connected to the capsule chamber and ending tangentially in the capsule chamber. Advantageously the air inlets end into the capsules chamber perpendicular to a middle plane of the base body. Preferably, the air inlets end in the circular cylindrical section of the capsule chamber. When air is sucked in through a mouthpiece of the dry powder inhaler which is in fluid communication with the capsule chamber, ambient air can be sucked into the capsule chamber through the air inlets such that a capsule is lifted and rotates in the capsule chamber.

In order to conduct ambient air to the air inlets of the base body it is particularly preferred if the dry powder inhaler comprises a mouthpiece arranged on top of the base body, wherein the mouthpiece comprises at least one, advantageously two air inlets, fluidly connected with the air inlets of the base body. Preferably, those air inlets of the mouthpiece are arranged on a lateral side of the mouthpiece. Advantageously, the inhaler body functions as an air buffer area wherein air is sucked into the capsule chamber during inhalation through the air inlets of the base body via the air inlets of the mouthpiece.

According to a preferred embodiment, the capsule receptacle is configured to receive a capsule with a volume in the range of about 400 to about 500 mm$^3$. Advantageously, such a capsule has a volume of 437 mm$^3$. Preferably, the size of the capsule receptacle corresponds with the size of the capsule such that the capsule receptacle is only slightly bigger than the capsule to ensure that the capsule is held in the capsule receptacle when pushing the actuator buttons and piercing the capsule with the needles.

If is particularly preferred if the capsule chamber has a volume of about 2500 to about 3000 mm$^3$. By providing a capsule chamber with such a volume it can be ensured that the capsule can rotate efficiently during inhalation.

It is particularly preferred if the size of the capsule is in a proportion to the size of the capsule chamber in a range of 1:5 to 1:6.

Advantageously, the needles have a needle diameter of about 1.35 to about 1.85 mm. With such a needle diameter, the release of high dosage of dry powder can be insured.

According to another preferred embodiment of the dry powder inhaler, the needles have a cutting tip with a cutting tip angle with respect to a longitudinal axis of the needle in the range of about 20 to about 35°. Such a cutting tip angle can allow an accurate cutting of a shell of a capsule during piercing of the capsule without detaching the cut-out portion from the capsule shell. Therefore, the cut-out portion can be bent inwards in a hinged fashion.

It is particularly preferred if the needles have lateral cutting edges which are arranged in an angle in the range of about 25 to 35° with respect to an axis perpendicular to the longitudinal axis and lying in a plane parallel to the longitudinal axis.

Advantageously, the needles are symmetrical to a middle plane.

The object of the subject invention is furthermore solved by a dry powder inhaler according to the features of claim 25. Such a dry powder inhaler is characterized in that an intermediate air chamber is formed between the base body and the covering body, wherein the mouthpiece has an inhaling inlet fluidly connected to the capsule chamber and at least one mouthpiece air inlet arranged on a lateral outside of the mouthpiece and fluidly connected to the intermediate air chamber and wherein the base body has at least one base body air inlet being fluidly connected to the capsule chamber and to the intermediate air chamber and ending in the capsule chamber.

Preferably, the base body is connected to the covering body such that no or substantially no air can be sucked out of the capsule chamber at the joint surface between the base body and the covering body. It is particularly preferred if two actuator buttons are provided on opposing sides of the covering body movable between a normal position and a perforation position. Advantageously, the actuator buttons are closing the covering body in the normal position in a substantially airtight manner such that no or substantially no air can pass between the actuator buttons and opening edges of the openings which are configured to receive the actuator buttons. It is therefore particularly preferred that substantially no air can be sucked in between the covering body and the actuator buttons when the actuator buttons are in the normal position. In a preferred embodiment of the dry powder inhaler the at least one base body air inlet ends tangentially into the capsule chamber. Preferably, two base body air inlets are provided.

When a patient or user is using the dry powder inhaler, a capsule arranged in the capsule chamber can be pierced by moving the actuator buttons from the normal position into the perforation position along an actuation direction. After piercing the capsule, the actuator buttons are moved back into the normal position. When a patient or user is sucking in air through the inhaling inlet of the mouthpiece, a partial vacuum in the capsule chamber can be generated wherein air is sucked through the capsule chamber through the at least one base body air inlet generating an air flow that lifts the capsule in the capsule chamber and rotates the capsule in the capsule chamber such that dry powder contained in the capsule chamber can be dispersed.

Advantageously, the air sucked through the capsule chamber through the at least one base body air inlet can be directed from the mouthpiece air inlet and through the intermediate air chamber. By directing the air flow through the intermediate air chamber, a dry powder inhaler can be provided which offers less resistance at lower flow rates and comparatively more resistance at higher flow rates in contrast to a dry powder inhaler which has no such intermediate air chamber.

According to a preferred embodiment of the dry powder inhaler, the capsule chamber is circular cylindrical and comprises a hemi-spherical end-section having a capsule receptacle. The capsule receptacle can be arranged in an angle with respect to an actuation direction of the actuator buttons. Nevertheless, it is also possible that the capsule receptacle is arranged parallel to the actuation direction.

Preferably, the mouthpiece comprises a cylindrical protrusion configured to extend at least partially into the capsule chamber.

In a particularly preferred embodiment of the dry powder inhaler, the cylindrical protrusion of the mouthpiece extends into the capsule chamber wherein a lateral surface of the cylindrical protrusion is configured to sealingly abut on an inside surface of the capsule chamber.

Preferably, the cylindrical protrusion abuts such an the inside surface of the capsule chamber that substantially no air can be sucked out of the capsule chamber between the inside surface of the capsule chamber and the lateral surface of the cylindrical protrusion.

In another preferred embodiment of the dry powder inhaler, the base body comprises at least one base body duct overlapping with and in fluid connection with the mouthpiece air inlet, wherein the base body duct is fluidly connected to the intermediate air chamber and ends in the intermediate air chamber. Preferably, the base body duct is an opening in the base body overlapping with the mouthpiece air inlet.

Preferably, the base body comprises a cylindrical shoulder which is preferably oval and a base body plate which is preferably oval and arranged perpendicular to the cylindrical shoulder. Preferably, the base body plate defines an outside wall of the intermediate air chamber. Advantageously, the at least one base body duct is an opening in the base body plate overlapping with the mouthpiece air inlet such that the intermediate air chamber is fluidly connected to the mouthpiece air inlet.

In a preferred embodiment of the dry powder inhaler, the capsule chamber is attached to the base body plate and opens into the base body plate.

Further details and advantages of the invention can be taken from the following description, on the basis of which the embodiments of the invention that are represented in the Figures are described and explained in more detail.

Figure 11:
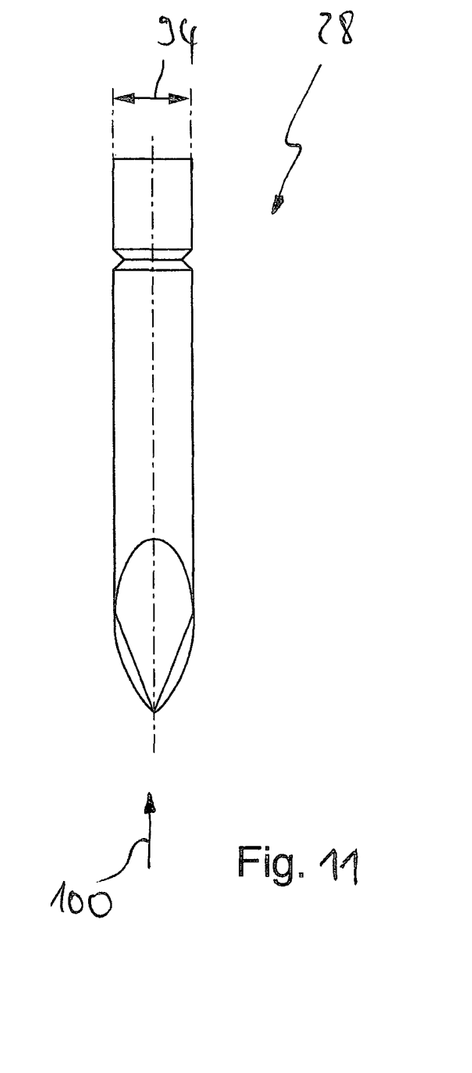
FIG. 11 a top view of the needle of FIG. 10.
Figure 12:
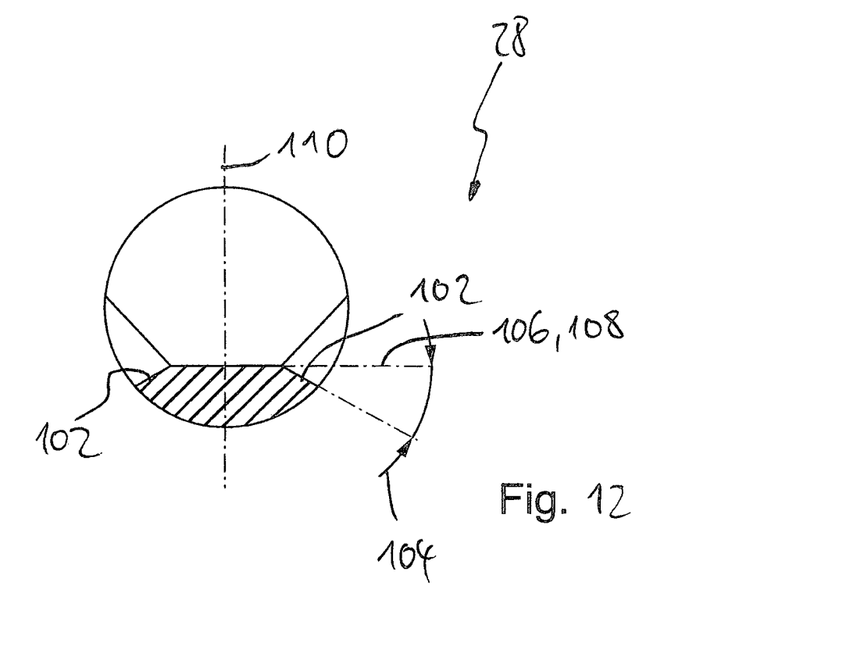
FIG. 12 a front view of the needle of FIGS. 10 and 11.
Figure 13:
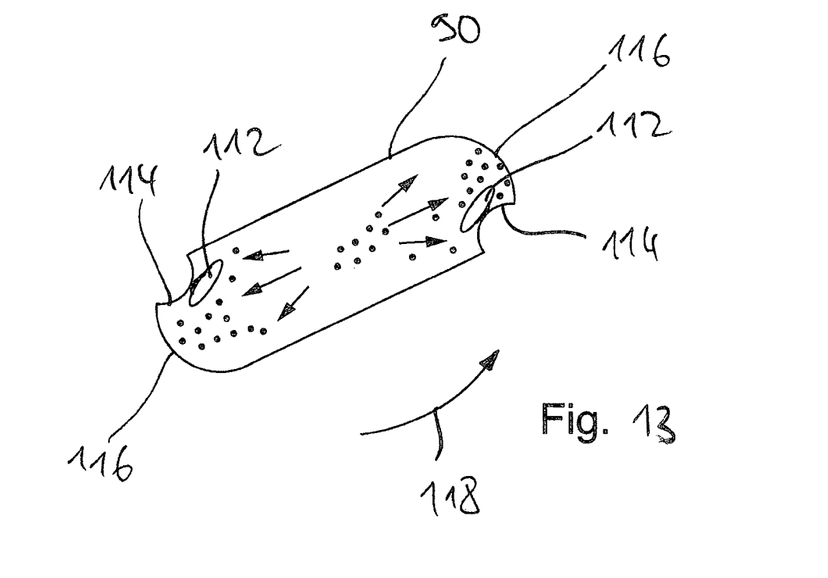
FIG. 13 a schematic view of a pierced capsule during inhalation.

FIGS. 1 to 12 show a dry powder inhaler 10 for a capsule containing dry powder (shown in FIG. 13). The dry powder inhaler 10 comprises a housing 12 having a base body 14 and a covering body 16. The dry powder inhaler 10 furthermore comprises a mouthpiece 18. The mouthpiece 18 has a mouth portion 20 having a central opening 22 for inhaling air that mixes with dry powder contained in a capsule arranged in the dry powder inhaler 10.

Figure 1:
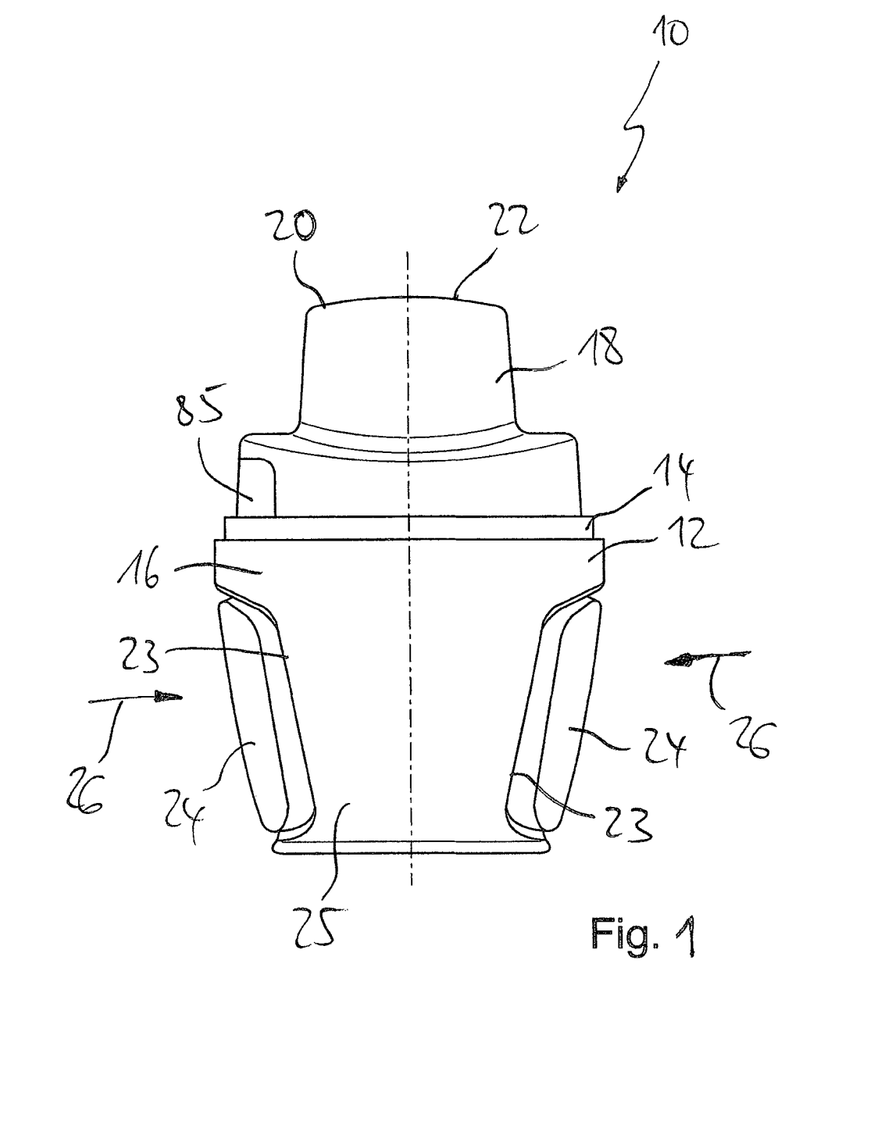
FIG. 1 a side view of a dry powder inhaler according to the invention.
Figure 2:
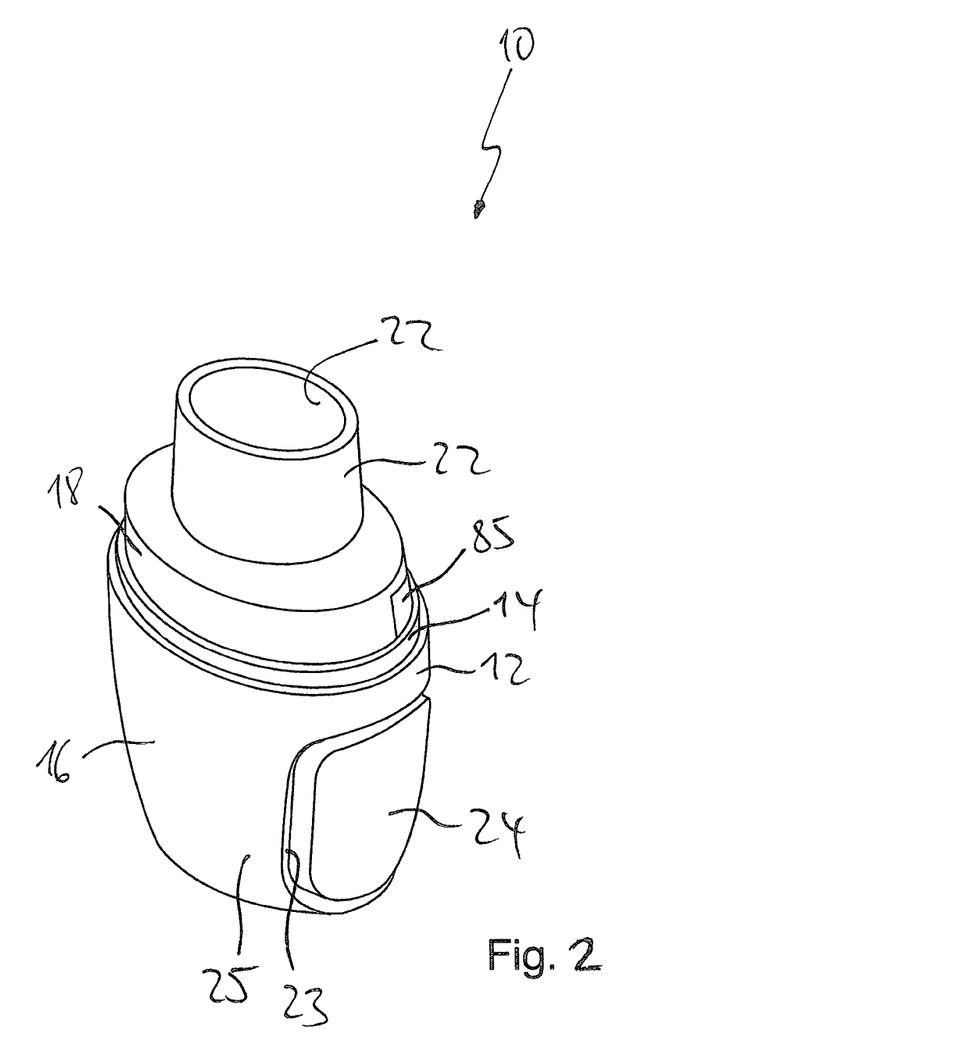
FIG. 2 a perspective view of the dry powder inhaler of FIG. 1.

The dry powder inhaler 10 comprises two actuator buttons 24 arranged on opposing sides of the housing 12 which are movable relative to the housing 12 towards each other along an actuation direction which is indicated by arrows 26 from a normal position to a perforation position to perforate a capsule arranged in the dry powder inhaler 10. The housing 12 comprises two openings 23 configured to receive the actuator buttons 24 such than an outside surface 25 of the housing 12 and the actuator buttons 24 is substantially flush when the actuator buttons 24 are in the normal position.

Figure 3:
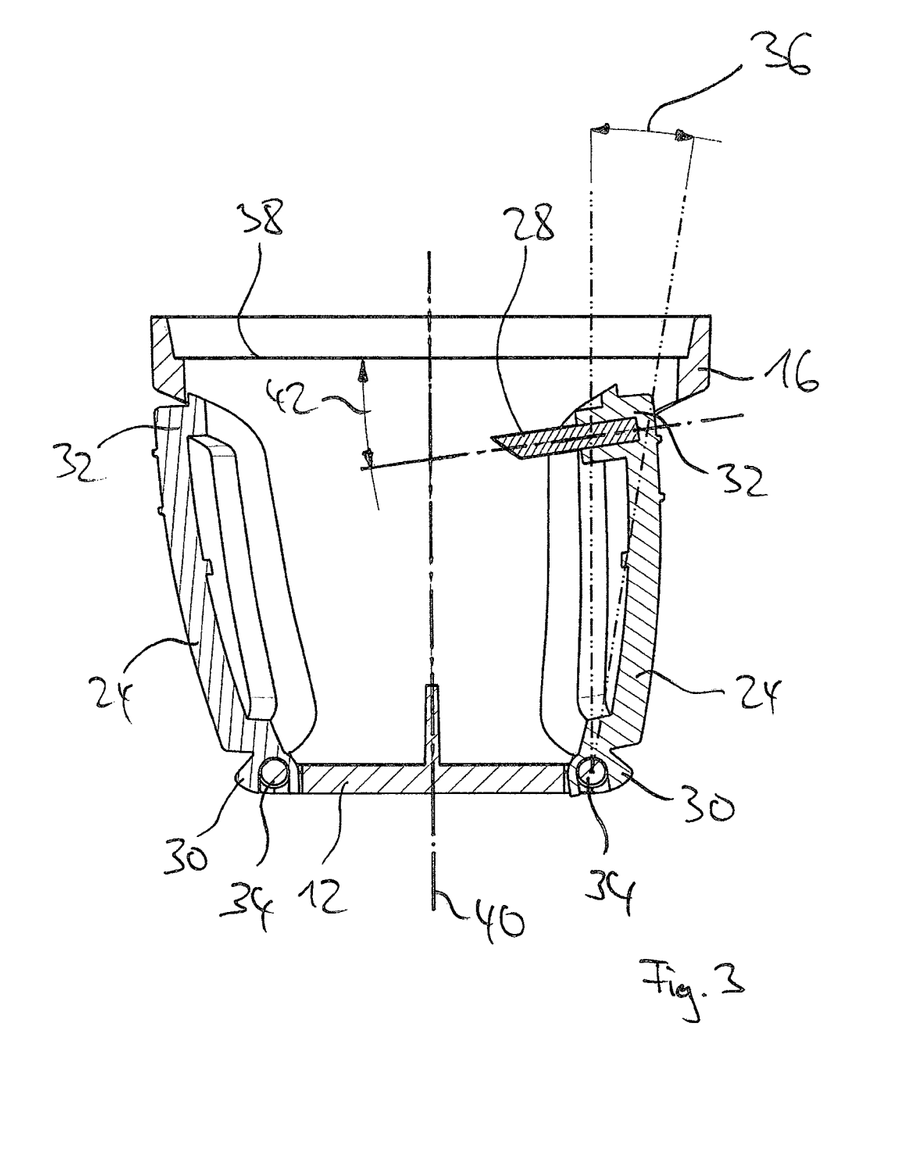
FIG. 3 a sectional view of a part of the dry powder inhaler of FIGS. 1 and 2

FIG. 3 shows a sectional view of a part of the dry powder inhaler 10 of FIGS. 1 and 2. Each actuator button 24 is attached the covering body 16, i.e. the housing 12, wherein a perforation needle 28 is provided being fixedly connected to an actuator button 24. FIG. 3 shows only one perforation needle 28 because the needles 28 are arranged with an offset concerning the cutting plane of FIG. 3.

A first end 30 of each actuator button 24 is connected to the housing 12, i.e. the covering body 16 in a lower portion of the housing 12. The perforation needles 28 are arranged in an area of a second free end 32 of the actuator buttons 24. This second free end 32 is spaced away from the first end 30. The second free end 32 of the actuator buttons 24 is movable from the normal position into the perforation position shown in FIG. 3 such that a tip of the perforation needle 28 is moved along a circular line.

The first end 30 of each actuator button 24 is pivotably attached to the housing 12 by use of a ball joint snap-on connection 34 pivoting around a pivot axis, wherein the actuator button is pivotable around a pivoting angle 36 of about 5° to 15°, preferably of about 10°. Accordingly, the perforation needles 28 are inclined with respect to a plane 38 which is perpendicular to a longitudinal axis 40 of the dry powder inhaler 10 in a perforation angle 42 of about 5° to 15°, preferably of about 10° when the actuator buttons 24 are in the perforation position.

The ball joint snap-on connection 34 comprises hemispherical protrusions (not shown in the drawings) arranged on the housing 12 and hemi-spherical recesses 44 (shown in FIG. 4) arranged on the actuator buttons 24, wherein the protrusions and recesses extend along the pivot axis and wherein the protrusions engage the recesses.

By arranging the two actuator buttons 24 on opposing sides of the housing 12 and connecting each actuator button 24 to the housing 12 at a lower portion of the housing 12, the actuator buttons 24 can be pre-loaded into the normal position by use of only one spring element.

Figure 4:
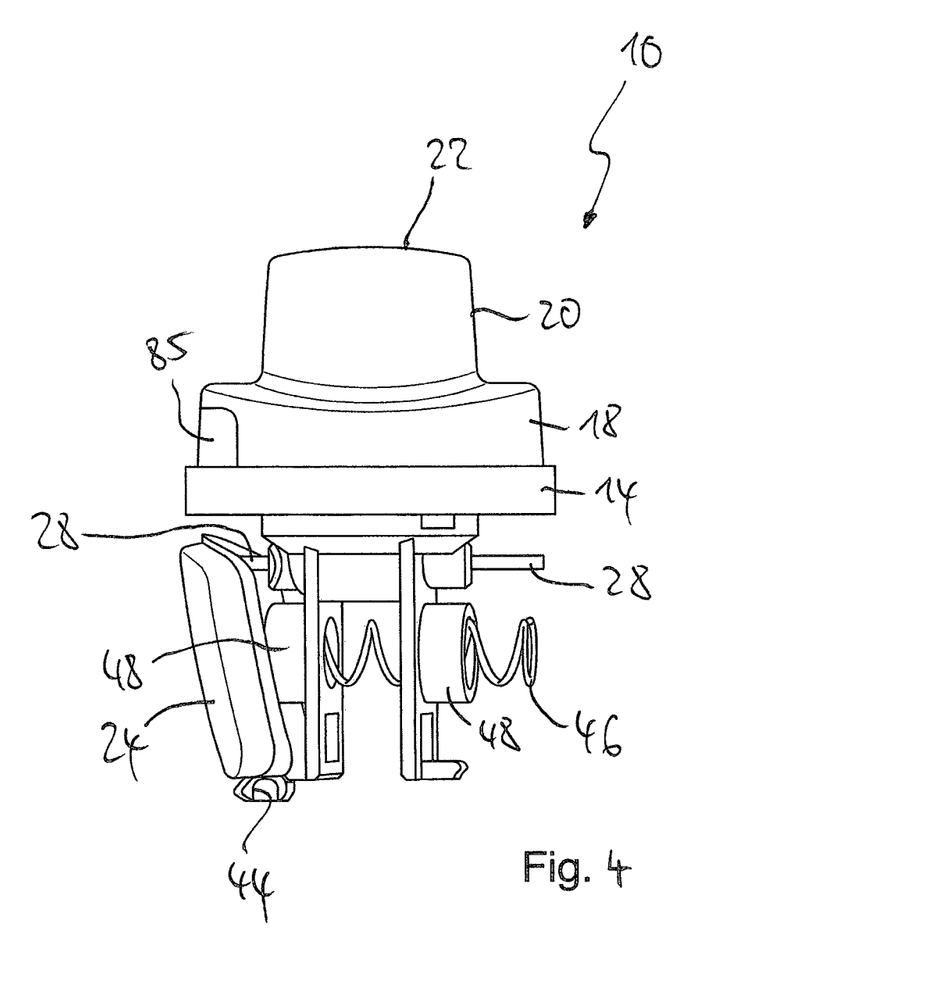
FIG. 4 a perspective view showing parts of the dry powder inhaler of FIGS. 1 to 3.

Such a spring element is shown in FIG. 4 which shows a perspective view with of parts of the dry powder inhaler. The dry powder inhaler 10 comprises a helical spring 46 arranged in shell-like spring-guiding members 48 of the base body 12 and acting upon the actuator buttons 24 such that the actuator buttons 24 are pre-loaded into the normal position against the direction depicted by arrows 26.

Figure 5:
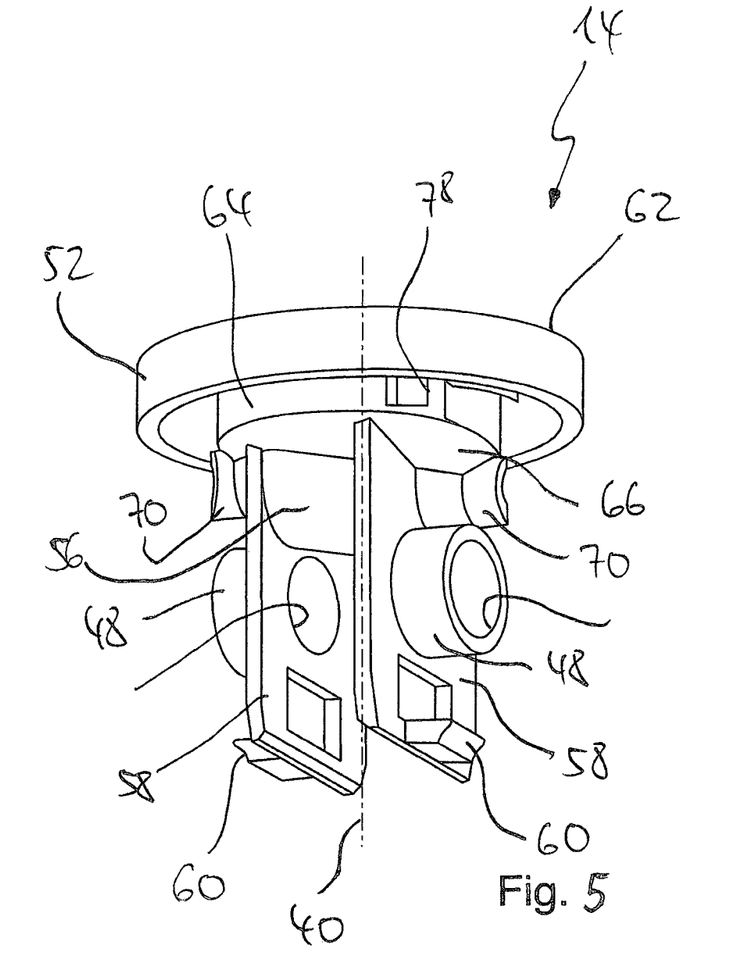
FIG. 5 a perspective view of a base body of the dry powder inhaler of FIGS. 1 to 4.
Figure 6:
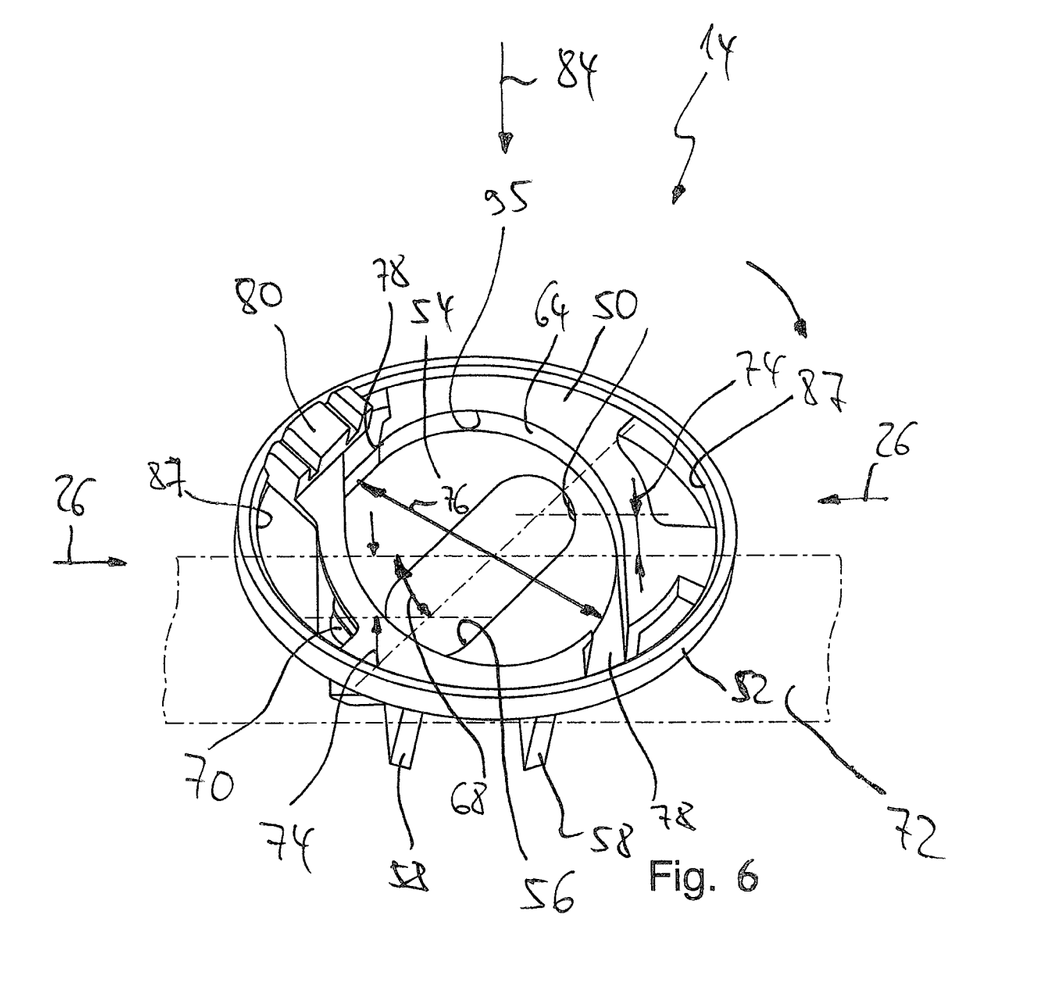
FIG. 6 a perspective top view of the base body of FIG. 5.
Figure 8:
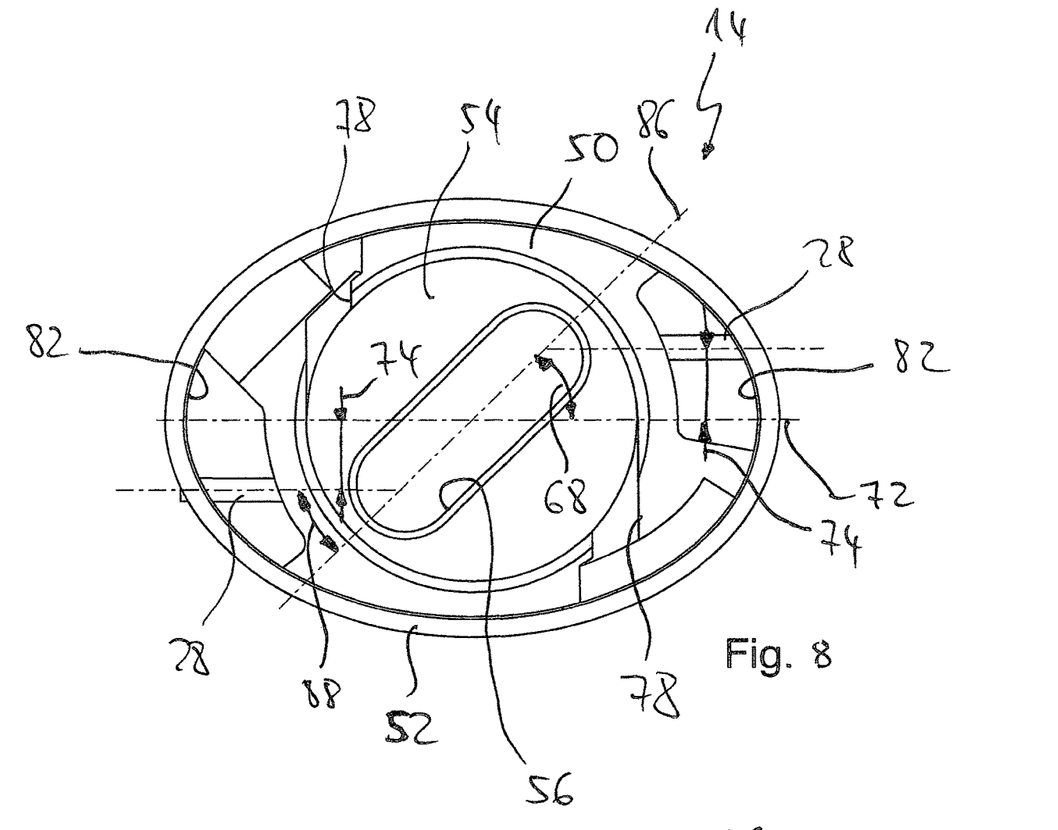
FIG. 8 a top view of the base body of FIGS. 5 and 6.

The base body 14 of the dry powder inhaler 10 which is made of one piece is shown in more detail in FIGS. 5 and 6. FIG. 8 furthermore shows a top view of the base body 14 of FIGS. 5 and 6. The base body 14 has an elliptical or oval base body plate 50 and an oval cylindrical shoulder 52 extending perpendicular to the base body plate 50 and connected to the base body plate 50. The base body 14 has a capsule chamber 54 having a capsule receptacle 56 for receiving a dry powder capsule and two downwardly extending plate members 58 that are substantially parallel to each other. The spring-guiding members 48 are arranged coaxially to the actuation direction 26 wherein the plate members 58 are arranged perpendicular to the actuation direction 26. At a free end of the plate members 58, bearing sections 60 for the actuator buttons 24 are provided.

The capsule chamber 54 is open towards an upper end portion 62 of the base body 14. The capsule chamber 54 has a circular cylindrical section 64 and a hemi-spherical or conical end section 66, wherein the capsule receptacle 56 is arranged in the hemi-spherical end section 66 of the capsule chamber 54. The capsule chamber 54 has a volume of about 2500 to about 3000 mm$^3$. The capsule receptacle 56 is arranged perpendicular to the longitudinal axis 40 of the dry powder inhaler 10.

The capsule receptacle 56 is furthermore arranged in an inclined angle 68 within the range of 40° to 50° with respect to the actuation direction 26. The base body 14 comprises two hollow needle guiding sections 70 configured to guide the needles 28 and being arranged perpendicular to the longitudinal axis 40 of the inhaler 10 and ending in the capsule receptacle 56. Those needle guiding sections 70 and the needles 28 are arranged parallel to the actuation direction 26 and spaced apart from a middle plane 72 of the base body 14 in a distance 74. The needles 28 are arranged on opposing sides of the middle plane 72.

According to another embodiment not shown in the drawings, the capsule receptacle 56 is not arranged in an inclined angle with respect to the actuation direction 26 but is parallel to the actuation direction 26. In that case the needle guiding sections 70 and the needles 28 are arranged parallel to the actuation direction 26 but are not spaced apart from the middle plane 72 of the base body 14. With this embodiment a capsule arranged in the capsule receptacle 56 can be pierced directly in the hemi-spherical end-section of the capsule.

The circular cylindrical section 64 has a diameter 76 which is bigger than the length of the capsule receptacle 56. The size of the capsule receptacle 56 corresponds with the size of the capsule such that the capsule receptacle 56 is only slightly bigger than the capsule to ensure that the capsule is held in the capsule receptacle 56 when pushing the actuator buttons 24 and piercing the capsule with the needles 28. Preferably, the capsule receptacle 56 is configured to receive a capsule with a volume in the range of about 400 to about 500 mm$^3$. Nevertheless, smaller capsules in the range of about 150 to 400 mm$^3$ are also possible. In any case, it is preferred if the capsules have a volume in a proportion to the volume of the capsule chamber in a range of 1:5 to 1:6.

The base body 14 furthermore has two base body air inlets 78 in the area of the cylindrical shoulder 52 which are ending tangentially into the capsule chamber 54 and are arranged perpendicular to the middle plane 72 of the base body 14. The mouthpiece 18 is fastened to the base body 14 via a hinge. A lower part of the hinge is depicted in FIG. 6 and having the reference numeral 80. The base body 14 also comprises two base body ducts 82.

Figure 7:
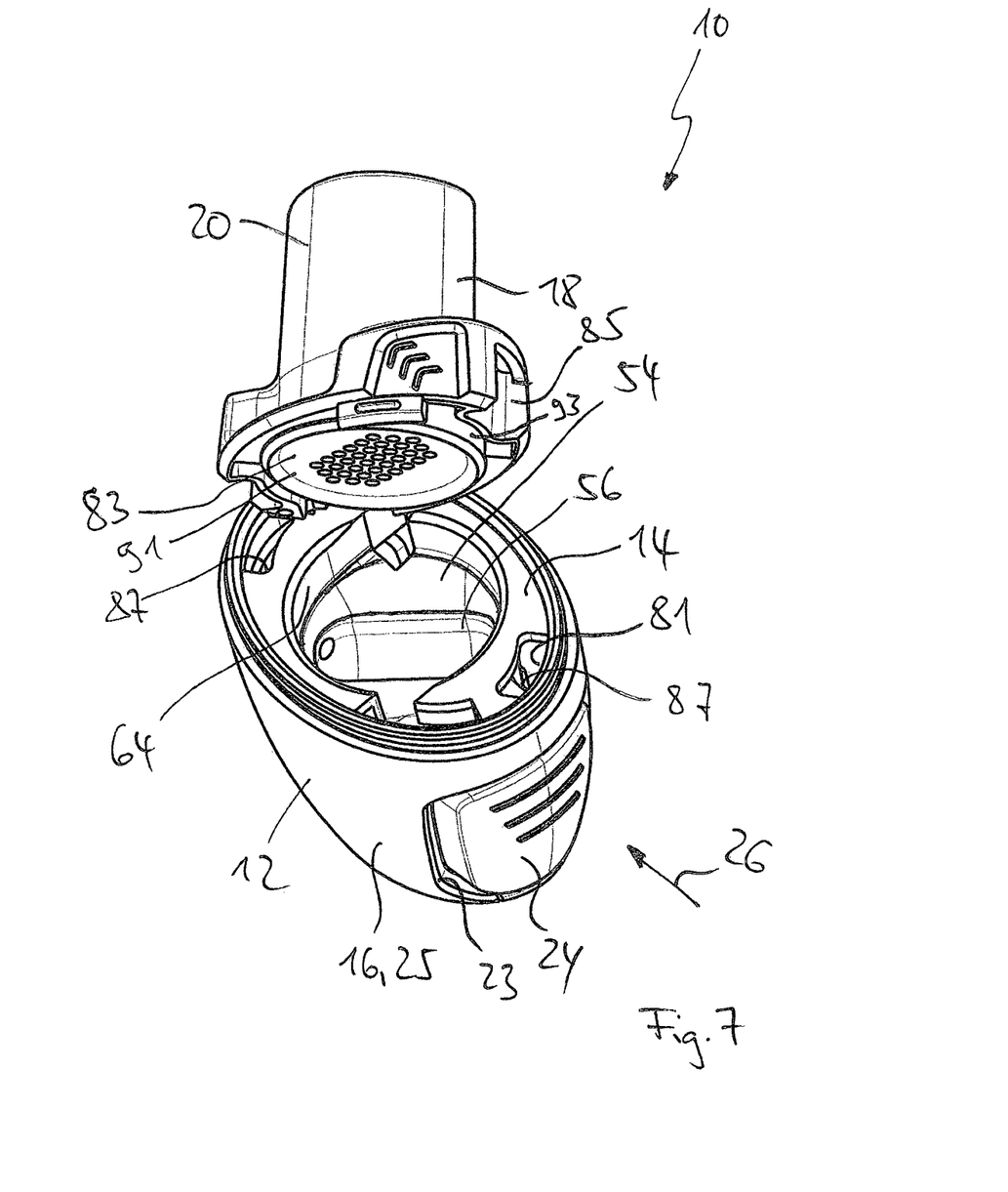
FIG. 7 a top perspective view of a dry powder inhaler of FIGS. 1 to 4 in an open position.

Between the base body 14 and the covering body 16 of the housing 12 an intermediate air chamber 81 is formed. The central opening 22 of the mouthpiece 18 functions as inhaling inlet and is fluidly connected to the capsule chamber 54 via a perforated plate 83 as shown in FIG. 7. The mouthpiece 18 has two mouthpiece air inlets 85 on a lateral outside of the mouthpiece which are fluidly connected to the intermediate air chamber 81.

The base body air inlets 78 are also fluidly connected to the intermediate air chamber 81 and to the capsule chamber 54. The base body comprises two base body ducts 87 overlapping with and in fluid connection with the mouthpiece air inlets 85. The base body ducts 87 are also fluidly connected to the intermediate air chamber 81 and end in the intermediate air chamber 81.

On the side facing away from the mouth portion 20, the mouthpiece 18 comprises a cylindrical protrusion 91 configured to extend at least partially into the capsule chamber 54. The perforated plate 83 is arranged in an end-section of the cylindrical protrusion 91. A lateral surface 93 of the cylindrical protrusion 91 is configured to sealingly abut on an inside surface 95 of the capsule chamber 54 such that substantially no air can pass between the inside surface 95 of the capsule chamber 54 and the lateral surface 93 of the cylindrical protrusion.

FIG. 8 shows a top view of the base body 14 of FIG. 6 when viewing in the direction of arrow 84 in FIG. 6. The capsule receptacle 56 has a longitudinal axis 86 which is arranged in an inclined angle 68 within the range of about 40° to about 50° with respect to the actuation direction 26 or the middle plane 72. The needles 28 are piercing a capsule which can be arranged in the capsule receptacle 56 in an angle 88 with respect to the longitudinal axis 86 of the capsule receptacle 56 or the capsule.

Figure 9:
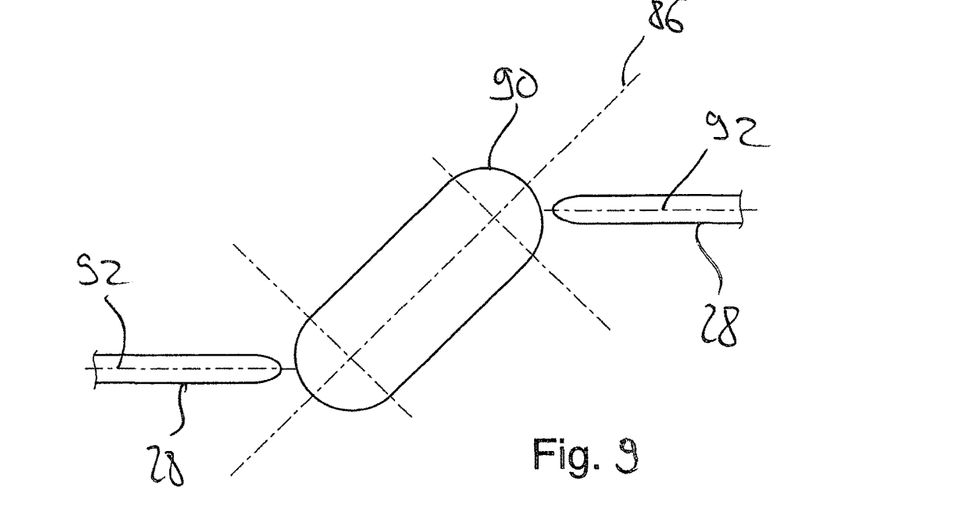
FIG. 9 a capsule and two needles in a piercing position.

Such a capsule 90 is shown in FIG. 9. The longitudinal axis 86 of the capsule 90 is arranged to a longitudinal axis 92 of the needles 28 in the angle 88.

Figure 10:
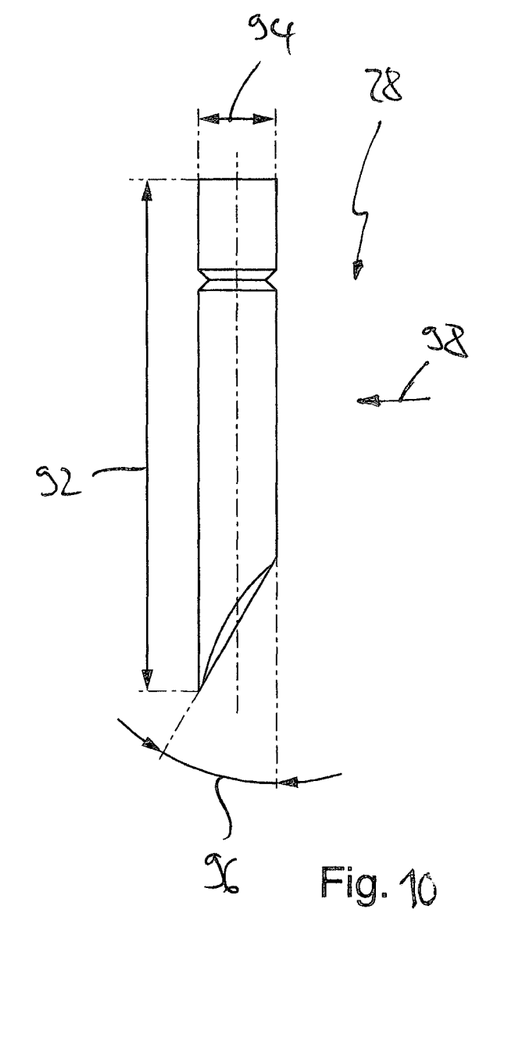
FIG. 10 a side view of a needle of the dry powder inhaler of FIGS. 1 to 4.

FIG. 10 depicts a side view of one of the needles 28 of the dry powder inhaler 10. The needles 28 have a length 92, a needle diameter 94 and a cutting tip angle 96. The needle diameter 94 is in the range of about 1.35 to about 1.85 mm wherein the cutting tip angle 96 is in the range of about 20° to 40°.

FIG. 11 shows a top view of the needle 28 of FIG. 10 when looking into the direction of arrow 98 in FIG. 10.

FIG. 12 shows a partial cross-section A-A of the needle 28 of FIGS. 10 and 11 in a front view when looking into the direction of arrow 100 in FIG. 11.

The needles 28 have lateral cutting edges 102 which are arranged in an angle 104 in the range of about 25 to 35° with respect to an axis 106 perpendicular to the longitudinal axis 92 of the needle 28 and lying in a plane 108 parallel to the longitudinal axis 92. The needles 28 are symmetrical to a middle plane 110.

The dry powder inhaler 10 functions as follows:

In order to insert a dry powder capsule 90 into the capsule receptacle 56 of the base body 14, the mouthpiece 18 can be pivoted into an opening position via the hinge 80 as shown in FIG. 7. After insertion of the capsule 90, the mouthpiece 18 is pivoted back into a closed position as depicted in FIGS. 1 and 2. In order to pierce the capsule 90, the actuator buttons 24 are pressed against the force of the helical spring 46 into the actuation direction 26.

The cutting tip angle 96, the lateral cutting edges 102 and the arrangement of the capsule receptacle 56 and the needles 28 provide for an accurate cutting of a shell of the capsule 90 during piercing of the capsule 90 without detaching the cut-out portion from the capsule shell.

FIG. 13 depicts a schematic view of a pierced capsule 90 during inhalation. Cut-out portions 112 can be bent inwards into the interior of the capsule 90 in a hinged or flap-like manner.

Because of the comparably large needle diameter 94, comparably big openings 114 can be pierced into the capsule 90 in a transition area of the hemispherical ends 116 and the tubular middle section of the capsule 90.

When a patient or user is using the dry powder inhaler 10, a capsule 90 arranged in the capsule receptacle 56 can be pierced by moving the actuator buttons 24 from the normal position into the perforation position. After piercing the capsule 90, the actuator buttons 24 are moved back into the normal position. When a patient or user is sucking in air through the inhaling inlet 22 of the mouthpiece 18, a partial vacuum in the capsule chamber 54 can be generated wherein air is sucked into the capsule chamber 54 through the at least one base body air inlet 78 generating an air flow that lifts the capsule 90 from the capsule receptacle 56 into the capsule chamber 54 and rotates the capsule 90 in the capsule chamber 54 in the direction of arrow 118 as shown in FIG. 13 such that dry powder contained in the capsule 90 can be dispersed.

When sucking in air on the inhaling inlet 22 through the capsule chamber 54, air is directed from the mouthpiece air inlets 85 via the base body ducts 87 and through the intermediate air chamber 81 into the capsule chamber 54 via the base body air inlets 78.

Table 1 and Table 2 shown below show comparative tests of flow resistances of a dry powder inhaler 10 having an intermediate air chamber 81 and flow resistances of a dry powder inhaler without an intermediate air chamber 81.

TABLE 1 flow resistance at different air flow
inhaler with intermediate air chamber

| L/min, | Value | Unit |
| --- | --- | --- |
| 30 | 0.74 | kPA |
| 60 | 1.56 | kPA |
| 90 | 3.52 | kPA |
| 100 | 3.81 | kPA |

TABLE 2 flow resistance at different air flow
inhaler without intermediate air chamber

| L/min, | Value | Unit |
| --- | --- | --- |
| 30 | 0.82 | kPA |
| 60 | 2.16 | kPA |
| 90 | 3.83 | kPA |
| 100 | 4.02 | kPA |

By directing the air flow through the intermediate air chamber 81, a dry powder inhaler 10 can be provided which has less resistance at lower flow rates and more resistance at higher flow rates in contrast to a dry powder inhaler which has no intermediate air chamber 81.

Overall, an inhaler 10 with an intermediate air chamber 81 can be provided that has less flow resistance at typical lung capacities. When a user or patient has less lung capacity under about 60 L/min, a dry powder inhaler 10 can be provided with significantly less flow resistance in comparison to dry powder inhalers without such an intermediate air chamber 81.

Because of the arrangement of the capsule receptacle 56 and the needles 28, the capsule 90 can be pierced in a position that allows powder to be efficiently dispersed during the rotational movement in an inhalation process while providing little or almost no obstruction to the powder flow.

To sum up, a dry powder inhaler 10 is provided which allows for a highly efficient inhalation, especially for high dosage inhalation but it can also be used for lower dosage inhalation.

The invention claimed is:

1. A dry powder inhaler for a capsule containing dry powder, the inhaler comprising:
   a housing having a capsule receptacle;
   two actuator buttons arranged on opposing sides of the housing, wherein a first end of each actuator button is connected to the housing at a lower portion of the housing via a ball snap-on connection, wherein a plurality of pivot points are associated with the ball joint snap-on connections, and wherein each actuator button pivots around a respective pivot axis associated with a respective pivot point; and
   two perforation needles, each needle being fixedly connected to a respective actuator button and movable relative to the housing towards each other from a normal position to a perforation position along an actuation direction to perforate a capsule arranged in the capsule receptacle, wherein a first end of each actuator button is connected to the housing at a lower portion of the housing, and wherein a second free end of each actuator button is movable into the perforation position such that the perforation needle is moved along a circular line.

2. The dry powder inhaler of claim 1, wherein the first end of each actuator button is pivotably attached to the housing.

3. The dry powder inhaler of claim 1, wherein the actuator buttons are pivotable around a pivoting angle of 5 to 15°.

4. The dry powder inhaler of claim 1, wherein the ball joint snap-on connection comprises hemi-spherical protrusions arranged on the housing and hemi-spherical recesses arranged on the actuator buttons complementary to the hemi-spherical protrusions, wherein the protrusions and recesses extend along the pivot axis.

5. The dry powder inhaler of claim 1, wherein the perforation needles are arranged in an area of the second free end of each actuator button spaced away from the first end of the actuator button.

6. The dry powder inhaler of claim 1, wherein the dry powder inhaler comprises a spring element acting upon the actuator buttons such that the actuator buttons are pre-loaded into the normal position.

7. The dry powder inhaler of claim 1, wherein the housing comprises two openings configured to receive the actuator buttons such that an outside surface of the housing and the actuator buttons is substantially flush when the actuator buttons are in the normal position.

8. A dry powder inhaler for a capsule containing dry powder, the inhaler comprising:
a base body having a capsule receptacle;
two actuator buttons arranged on opposing sides of the base body; and
two perforation needles, each needle being fixedly connected to a respective actuator button and movable relative to the basebody towards each other from a normal position to a perforation position along an actuation direction to perforate a capsule arranged in the capsule receptacle, wherein the capsule receptacle is arranged in an inclined angle within the range of about 40° to about 50° with respect to the actuation direction.

9. The dry powder inhaler of claim 8, wherein the needles are arranged parallel to the actuation direction and spaced apart from a middle plane of the base body.

10. The dry powder inhaler of claim 8, wherein the capsule receptacle is arranged perpendicular to a longitudinal axis of the inhaler.

11. The dry powder inhaler of claim 8, wherein the base body comprises two hollow needle guiding sections configured to guide the needles, the needle guiding sections being arranged perpendicular to a longitudinal axis of the inhaler and ending in the capsule receptacle.

12. The dry powder inhaler of claim 8, wherein the base body is having a capsule chamber for rotation of a capsule.

13. The dry powder inhaler of claim 12, wherein the capsule receptacle is arranged in the capsule chamber and connected to the capsule chamber.

14. The dry powder inhaler of claim 12, wherein the capsule chamber is having a circular cylindrical section and a conical section wherein the capsule receptacle is arranged in the conical section.

15. The dry powder inhaler of claim 14, wherein the circular cylindrical section has diameter which is bigger than a length of the capsule receptacle.

16. The dry powder inhaler of claim 12, wherein the base body is having at least two air inlets connected to the capsule chamber and ending tangentially in the capsule chamber.

17. The dry powder inhaler of claim 16, wherein the dry powder inhaler comprises a mouthpiece arranged on top of the base body, wherein the mouthpiece comprises at least one air inlet fluidly connected with the air inlets of the base body.

18. The dry powder inhaler of claim 8, wherein the capsule receptacle is configured to receive a capsule with a volume in the range of 400 to 500 $mm^3$.

19. The dry powder inhaler of claim 8, wherein the capsule chamber has a volume of 2500 to 3000 $mm^3$.

20. The dry powder inhaler of claim 8, wherein the needles have a needle diameter of 1.35 to 1.85 mm.

21. The dry powder inhaler of claim 8, wherein the needles have a cutting tip with a cutting tip angle with respect to a longitudinal axis of the needle in the range of 20 to 35°.

22. The dry powder inhaler of claim 21, wherein the needles have lateral cutting edges which are arranged in an angle in the range of 25 to 35° with respect to an axis perpendicular to the longitudinal axis and lying in a plane parallel to the longitudinal axis.

23. The dry powder inhaler of claim 8, wherein the needles are symmetrical to a middle plane.

* * * * *